United States Patent
Clift et al.

(10) Patent No.: US 8,980,641 B2
(45) Date of Patent: Mar. 17, 2015

(54) METHOD FOR DETECTION OF CHEMICALS ON A SURFACE

(75) Inventors: Vaughan L. Clift, Houston, TX (US); Kristin L. Harriman, Houston, TX (US); Richard L. Pettys, Dickinson, TX (US); David M. Headley, Houston, TX (US); Tiffany M. Conerly, Santa Clara, CA (US)

(73) Assignee: Detectachem, LLC, Houston, TX (US)

( * ) Notice: Subject to any disclaimer, the term of this patent is extended or adjusted under 35 U.S.C. 154(b) by 0 days.

(21) Appl. No.: 12/309,704

(22) PCT Filed: Jul. 25, 2007

(86) PCT No.: PCT/US2007/016759
§ 371 (c)(1),
(2), (4) Date: Jan. 26, 2009

(87) PCT Pub. No.: WO2008/097268
PCT Pub. Date: Aug. 14, 2008

(65) Prior Publication Data
US 2009/0325300 A1 Dec. 31, 2009

Related U.S. Application Data

(60) Provisional application No. 60/833,727, filed on Jul. 26, 2006.

(51) Int. Cl.
*G01N 21/75* (2006.01)
*G01N 21/78* (2006.01)
(Continued)

(52) U.S. Cl.
CPC .............. *G01N 21/78* (2013.01); *G01N 21/94* (2013.01); *G01N 21/01* (2013.01); *G01N 35/00009* (2013.01); *C12Q 1/04* (2013.01); *G01N 2021/7733* (2013.01)
USPC .............................................. 436/165; 422/69

(58) Field of Classification Search
CPC .............. G01N 21/78; G01N 2021/78; G01N 2021/7733
See application file for complete search history.

(56) References Cited

U.S. PATENT DOCUMENTS

| | | | |
|---|---|---|---|
| 3,689,224 | A | 9/1972 | Agnew et al. |
| 3,697,227 | A | 10/1972 | Goldstein et al. |

(Continued)

OTHER PUBLICATIONS

Jenkins, T., et al., Development of Field Screening Methods for TNT, 2,4-DNT and RDX in Soil, Talanta, vol. 39, No. 4, 1992, pp. 419-428.

(Continued)

*Primary Examiner* — Yelena G Gakh
*Assistant Examiner* — Michelle Adams

(57) ABSTRACT

A method of rapidly detecting trace materials including biohazards, toxins, radioactive materials, and narcotics in situ is disclosed. A corresponding apparatus is disclosed. A trace of the material is collected on a pad of the card component, collected by swiping the pad on suspected surface or exposure to the suspected air volume. A novel card component is disclosed that when inserted in a chemical detection unit (CDU), releases reaction chemicals from flexible walled capsules in desired sequence. The exposed pad containing trace material and chemicals are heated in the chemical detection unit to produce a spectral pattern that is analyzed by the optical electronics in the CDU and results are displayed, stored and/or transmitted over a communications network.

10 Claims, 8 Drawing Sheets

(51) Int. Cl.
*G01N 21/94* (2006.01)
*G01N 21/01* (2006.01)
*G01N 35/00* (2006.01)
*C12Q 1/04* (2006.01)
*G01N 21/77* (2006.01)

(56) References Cited

U.S. PATENT DOCUMENTS

| | | | |
|---|---|---|---|
| 3,713,779 A | | 1/1973 | Sirago et al. |
| 3,726,645 A | | 4/1973 | Kaczmarek |
| 3,740,196 A | | 6/1973 | Stroterhoff et al. |
| 3,748,098 A | | 7/1973 | Dutch |
| 3,966,412 A | | 6/1976 | Stroterhoff |
| 4,428,907 A | | 1/1984 | Heijenga et al. |
| 4,788,039 A | | 11/1988 | Glattstein |
| 4,918,025 A | | 4/1990 | Grenner |
| 4,965,047 A | * | 10/1990 | Hammond ............ 422/58 |
| 5,035,860 A | | 7/1991 | Kleingeld et al. |
| 5,035,862 A | | 7/1991 | Dietze et al. |
| 5,094,816 A | | 3/1992 | Ishizaka et al. |
| 5,480,612 A | | 1/1996 | Margalit |
| 5,648,047 A | | 7/1997 | Kardish et al. |
| 5,804,141 A | | 9/1998 | Chianese |
| 5,824,268 A | | 10/1998 | Bernstein et al. |
| 5,859,375 A | * | 1/1999 | Danylewych-May et al. ............ 73/864.71 |
| 5,935,862 A | | 8/1999 | Novak |
| 6,077,711 A | * | 6/2000 | Singer ............ 436/66 |
| 6,228,657 B1 | | 5/2001 | Genovese et al. |
| 6,613,576 B1 | | 9/2003 | Rodacy et al. |
| 6,701,776 B2 | | 3/2004 | Stetter |
| 7,036,388 B1 | * | 5/2006 | Genovese et al. ......... 73/863.12 |
| 7,267,799 B1 | * | 9/2007 | Borich et al. ............ 422/82.05 |
| 2002/0142301 A1 | * | 10/2002 | Hovig et al. ............ 435/6 |
| 2003/0129767 A1 | | 7/2003 | Bautista et al. ............ 436/178 |
| 2004/0224354 A1 | * | 11/2004 | Kambara et al. ............ 435/6 |
| 2004/0265169 A1 | | 12/2004 | Haas et al. |
| 2005/0064601 A1 | | 3/2005 | Haas |
| 2005/0101027 A1 | | 5/2005 | Haas |
| 2005/0181517 A1 | * | 8/2005 | Chandler et al. ............ 436/169 |
| 2006/0062689 A1 | | 3/2006 | Kirollos et al. |
| 2006/0092030 A1 | * | 5/2006 | Povenmire ............ 340/601 |
| 2007/0003435 A1 | | 1/2007 | Haas et al. |

OTHER PUBLICATIONS

Yinon, Jehuda, et al., "The Analysis of Explosives", Pergamon Press, 1981, pp. 29-293.
Meng, H. et al., "Gunshot Residue Analysis—A Review" J.Forensic Sci, 1997; 42(4):553-570.
Hiley, R.W., "Investigations of Thin Layer Chromatographic Techniques Used for Forensic Explosives Analysis in the Early 1970s", Journal of Forensic Sciences. JFSCA, vol. 38, No. 4, Jul. 1993, pp. 864-873.
Lloyd, J.B.F., "Detection of Microgram Amounts of Nitroglycerin and related Compounds", Journal of Forensic Science Society, 1976, vol. 7, Issue 4, p. 198.
Baytos, J.F., "Field Spot-Test Kit for Explosives", Los Alamos National Laboratory, NM, USA, Jul. 1991 NTIS Publication #LA-12071-MS DE91015321.
Nam, S.I., "On-Site Analysis of Explosives in Soil: Evaluation of Thin-Layer Chromatography for Confirmation of Analyte Identity," Cold Regions Research and Engineering Laboratory, U.S. Army Corps of Engineers, Hanover, NH. Special Report, 1997.
Malotky, L., et al., "Explosive Analysis Kit," Proceedings, 1st Symposium on Analysis and Detection of Explosives, FBI Academy, Quantico Virginia, 1983, pp. 63-65.
Crockett, A., et al., "Field Sampling and Selecting On-Site Analytical Methods for Explosives in Soil" U.S. EPA, Project Summary EPA/540/R-97/501, National Exposure Research Laboratory, 1996.
Jenkins, Thomas F. et al., "Development of Field screening methods for TNT, 2,4-DNT and RDX in Soil", US Army Cold Regions Research and Engineering Laboratory, Hanover, New Hampshire, U.S.A. Talanta, vol. 39, No. 4. pp. 419-428, 1992, Duplicate with #2.
Parker, R.G., et al., "Analysis of Explosives and Explosive Residues", Journal of Forensic Sciences, Jan. 1975, vol. 20, No. 1.
Lisa Thiesan, David Hannum, Dale W. Murray, and John E. Parmeter. Nov. 2004. "Survey of Commercially Available Explosives Detection Technologies and Equipment 2004" Sandia National Laboratories.
Jay B. Fox. "Kinetics and mechanisms of the Griess reaction." Anal. Chem., 1979, 51 (9), pp. 1493-1502 . DOI: 10.1021/ac50045a032.
Dexter McRae, Wallace Haywood, Jonathan Powell, and Betty Harris. Jan. 1995. "High Explosive Spot Test Analyses of. Samples from Operable Unit (OU) 1111." UC-902 and UC-901. Los Alamos National Laboratories.
"Opportunities to Improve Airport Passenger Screening with Mass Spectrometry" 2004. Committee on Assessment of Security Technologies for Transportation, National Research Council. ISBN: 0-309-53299-X.

* cited by examiner

METHOD FOR DETECTION OF CHEMICALS ON A SURFACE

CLAIM TO EARLIER PRIORITY DATE

Date of the provisional patent application No. 60/833,727, filed on Jul. 26, 2006.

CROSS-REFERENCE TO RELATED APPLICATIONS

The Provisional patent application No. 60/833,727, filed on Jul. 26, 2006. The Provisional patent application is fully incorporated herein by reference.

STATEMENTS REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

The invention described herein relates generally to a method and apparatus for the detection of chemicals and biological agents. More specifically, it relates to a handheld electronic device and a card that can be used to collect and qualify or quantify chemicals in the environment. The invention is composed of two components, an electronic device with an optical system that can read, interpret and display a range of colors developed on a pad and a card containing said pad and incorporating liquid reagent capsules that can be activated in a controlled sequence, heated, or dried, and used to generate a pattern of colors specific to a limited range of chemicals.

2. Description of the Related Art

There is a desperate need for an improved method for detecting trace levels of certain chemicals. This is best exemplified by the recent terrorist bombings that have occurred in many countries across the globe.

Thousands of soldiers and civilians have been killed and tens of thousands wounded by what are commonly known as Improvised Explosive Devices or IED's. They range from homemade explosives formed from commercially available compounds such as peroxide and acetone that were used in the second set of London bombings in 2006; to more sophisticated devices made from virtually undetectable explosives like "Semtex" and incorporating explosive formed charges.

The latter has proved to be a particularly effective killing tool in which high explosive is place below a shaped metal disk. A mobile phone or wired detonator is embedded in the explosive, which is then detonated from a remote location. The metal disk melts by the explosion and forms a liquid projectile capable of penetrating inches of steel armor plating.

Despite the impression created by various sources in public mind, there is no way to detect these explosive devices once made and hidden by the roadside. As reported by a Department of Justice Study, the variety of high explosive used by the terrorists do not produce a vapor and cannot be detected by vapor based chemical sensors that are sometimes referred to as "sniffers" or by canine units.

Furthermore there is no way to effectively detect or block the use of the mobile phone as an effective detonator. In addition, the "Humvees" and like vehicles used for protecting soldiers, cannot carry sufficient armor plating to prevent penetration by the explosive formed charges. In short, we have no effective weapon against these devices.

The matter is further complicated by the peroxide types of explosives where the components are found in nail polish and cleaning fluid. Though these compounds are easily detected by vapor, they are ubiquitous making vapor detection useless.

In a significant but less dramatic setting we lack effective portable devices for identifying traces of many other compounds such as narcotics and biological agents. Biological agents range from those organisms that could be used for bio-terror such as Anthrax spores, to important causes of food poisoning. Several incidents have occurred recently with the contamination of spinach and peanut butter where a hand held portable detector would have permitted more rapid identification and eradication of the source.

It is argued that X-ray screening of baggage is an effective deterrent to those who would try to bomb a plane but it is equally apparent that detonation of a high explosive anywhere in the airport terminal would cause as much death and disruption as detonating the explosive on the plane.

Recent events in Glasgow, Scotland illustrated this whereby the explosive device was in a car that drove into the airport terminal and would not have been detected by existing methods. Use of a hand held portable device would permit establishing a "presence" for security personnel outside the confines of the baggage screening areas providing an improved deterrent.

For trace chemical detection there are physical methods and chemical methods. Physical methods involve the interaction of the vaporized molecule with an electronic detector. One common method referred to as Ion Mobility Spectroscopy or IMS is as follows. A sample is collected onto a swipe pad. The pad is then placed in a powerful electric field or near a radiation source and the sample molecules are broken up into ions, which are smaller electrically charged fragments. These ions are then electrically accelerated into a tube against a flow of inert gas. The gas slows the ions down and they fall onto electronic detectors. How far they progress down the tube is determined by the ion's size and charge.

If a sample of TNT is collected, ionized and passed down the tubes, its component parts will fall onto the detectors at specific locations which are stored by the machine. If an unknown compound thought to be TNT is collected and ionized, and if the gas flow rate and electrical acceleration are not altered, then the particles should fall in the same locations in similar proportions and the machine will detect it as TNT.

These machines are extremely sensitive and powerful laboratory tools. However, they do not perform as well when used a screening tool due to fluctuations in atmospheric pressure, high concentrations of benign compounds, and the overall complexity of the device. These common variables cause the device to alarm when there is no explosive present or worse yet, miss a real explosive. In addition these devices require a gas supply, are heavy, expensive, and require up to 20 minutes of calibration and warm-up time before use.

A further physical method involves the use of a selective polymer to bind the explosive as the vapor passes across a sensor. This binding induces physicals change such as how it interacts with light or a microscopic increase in weight, which is then detected electronically. These devices have also proved ineffective in real world settings because there are millions of similar molecules in the environment. Some of these molecules are present in very high concentrations, and these "like" compounds non-specifically bind to the polymer and are detected or block the detection of the real agent.

To be effective in detecting many of the explosives, the sample must first be collected onto a swipe and then vaporized to travel across the sensor. To be at all effective, the binding chemicals must be able to bind only a very limited subset of molecules in a narrow range of concentration. A large sample of real compound will overwhelm the detector and require the device to be taken out of service and cleaned before continued use.

All of the physical methods require large, less portable machines, frequent calibration, extensive training and are generally expensive; costing more than $US 30,000 per unit. Though the actual analysis may take only seconds, the warm up time and calibration and repeat calibration commonly require 30 minutes to run 10 samples.

At times, for effective detection in existing methods, samples must be diluted to the effective detection range of the device, requiring preceding knowledge of the sample or repeated testing, as well as advanced expertise in this procedure.

These devices are very prone to error if moved or exposed to varying temperatures. Most systems have electrical requirements of 120 VAC and have significant consumables such as gas canisters and replacement sensors.

Chemical methods are less varied. Essentially, for the detection of explosive compounds, these methods all use a similar group of chemicals that have been published in chemistry texts for decades. These chemicals react in a liquid medium with certain functional groups on the explosives and produce an observable color change.

Similar color chemistry methods exist for narcotics and many biological molecules. In addition, specific antibodies can be labeled with a color tag and bound to the target molecules in a liquid medium. The most common example of which is the ubiquitous urine pregnancy test.

Until the present invention, chemical methods were both hazardous to perform and technically difficult to execute. They required the application of caustic and acidic compounds and heat to the test pad to produce subtle color changes that were difficult to interpret correctly by eye. Existing embodiments of the method involve the spraying on of reagents, dropping of reagents from a dropper bottle or the crushing a glass ampoule.

In some versions, the operator must adjust the procedure based on initial results. In other embodiments, operators must time the procedure carefully and ignore specific colors even if they are the correct color but develop at the wrong time. All the existing embodiments are read by human eye and are subject to error from individual color perception, ambient lighting and temperature conditions.

By way of example, one such existing color chemistry method involves the spraying of the first reagent onto a paper swipe. If no color develops or if the color is not from a selected limited grouping, then a second reagent is sprayed. Depending on the timing and color that then may be produced, a third reagent may be added. If left, the paper swipe will develop a color change itself, which must be ignored. All these changes are dramatically affected by the accuracy of spraying and the ambient temperature.

In another embodiment, the user must add drops of solution from a bottle. A timer controls the heat reaction and a pink or orange coloration indicates a positive result for some explosives, however, gray and purple colors do not. Unfortunately these colors may be produced in the presence of common compounds such as red wine or ink, and incorrectly interpreted as a positive result. If no pink or orange color develops, the second reagent is added and the heat reapplied. Again, if particular colors develop it is a positive detection, but the presence of other colors are not. The interpretation of these colors, particularly in strong or weak lighting conditions, can completely obfuscate a positive result. Additionally, the reagents deteriorate in the bottles with exposure to air, and are extremely astringent, requiring the operator to wear personal protective equipment at all times, such as safety goggles and gloves.

BRIEF DESCRIPTION OF THE SEVERAL VIEWS OF THE DRAWINGS

A better understanding of the present invention can be obtained when the following detailed description of some embodiments is considered in conjunction with the drawings of the above noted application and the following drawings in which.

DETAILED DESCRIPTION OF THE INVENTION

The present invention alleviates the above noted problems by providing a simple, hand held, battery powered, sensitive and specific unit requiring no external calibration, ability to work in a wide range of environments, with a broad dynamic range and "plug-and-play" type operation. The flexible capsules contained in the card safely enclose and protect the reagents. Once swiped on a surface and placed in the machine, the device controls the sequence of fluid addition and heating. The optical assembly provides controlled illumination at specific wavelengths, any of which can be turned on separately by the controlling software.

The detector incorporates software configurable color filters and detects specific wavelengths in and beyond the human-visible spectrum, permitting an objective and sensitive measurement of color. If desired, the device can work fluoroscopically using different illuminating and detecting wavelengths.

Figure 1:
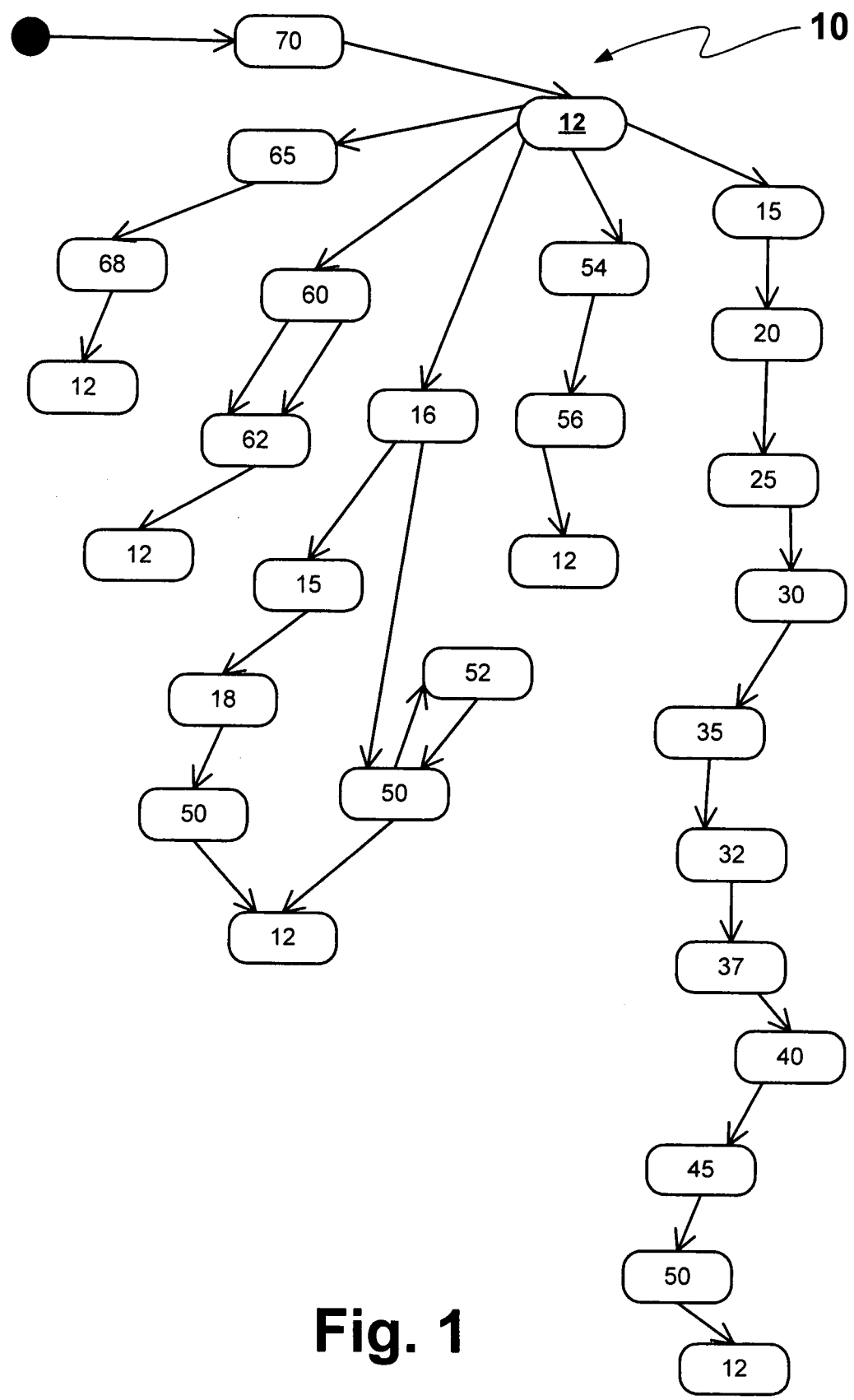
FIG. 1 is an overview flowchart of the method of operation of the Chemical Detection Unit with the card component.

With reference to FIG. 1 is an overview flowchart 10 of the method of operation of the Chemical Detection Unit (CDU) with the card component. When the CDU is powered up, it goes through its boot-up routine and performs hardware self-check 70. Upon power-on of the device, the system boot-up procedure incorporates self-diagnostic software tests to determine the status and usability of important device subsystems. If no sub-system failures or errors are detected, the Home Menu 12 will be displayed for user interaction. If an error is detected, the user will be alerted and provided with mitigation instructions. Various device settings are configurable by the user at run-time. The Settings Menu 65 provides the user with a list of user-modifiable settings 68, as well as access to diagnostic status for selected subsystems of the device. If operation help is necessary, a help menu 54 is presented and help display 56 menu appears.

Still referring to FIG. 1, when the test option is selected the CDU prompts for a scan of the barcode 15 and the user scans the barcode of the card component. If the scan is valid, the card component for testing is inserted into the CDU where its presence is detected. The optical system reads the initial color 25 corresponding to the spectral pattern of the card component after collecting an unknown trace materials sample on a pad of a flexible card component but prior to initiating the detection process. This reading is generally used for color bias correction. A sample of the unknown trace material is collected on the pad of the card component. Reaction of the unknown trace materials sample collected on the pad is initiated with liquid reagents and dissolve compounds contained in at least one flexible walled capsule embedded in the card component, wherein the reaction is initiated after inserting the card in a chemical detection unit causing walls of the capsules to yield to fluid flow, establishing fluid communication between the capsules and the pad. This is accomplished by releasing chemicals and other contents of the first capsule and applying heat 30 stimulates the reaction with the unknown trace material. The fluid communication may be established via specific paths like grooves or similar structural means, or using wicks. Further, chemicals from the capsules may be released in a fashion to react in spatially distinct regions of the pad or the regions may be temporally separated for chemical reactions. The spectral pattern is observed and recorded 35. The spectral pattern may correspond to toxic chemicals, explosives, biological agents, and/or radioactive materials in the visible spectrum or in the invisible spectrum. The optical analysis is able to perform analysis over a broad spectrum including ultraviolet and infrared regions of the spectrum. In this embodiment the color pattern may be associated with a spectral pattern in a database and the unknown trace material is identified. In another embodiment a second chemical from a second capsule 32 may be released on to the pad and heat is applied. This may result in a second spectral pattern 37 developed on the pad. The color pattern is read and data is stored 40. The stored data is analyzed using data comparison algorithms 45 and the spectral pattern is associated with known trace material spectral patterns and the detection results are displayed 50.

Still referring to FIG. 1, the chemical reaction stimulation may be accomplished by applying controlled heat to the entire pad, regions of the pad, or combinations thereof. Likewise, stimulation may also be accomplished by applying optical radiation.

If download option for downloading data from the CDU to a computer or other device is selected, a download target menu 60 is presented to the user. The download target may be a computer or an SD card or any other suitable device. A transmit data is requested 62 and after the transmission is successfully completed the user is directed to the main menu.

If the review of test result data is desired a prompt to scan or review results 16 is presented. If scan option is selected, trigger barcode reading prompt 15 is issued. The corresponding data for the barcode ID is searched 18 and card results 50 are displayed and the user is taken back to the main menu. If review option is selected, the results for each bar coded card 50 are presented upon request. After completing the review the user is taken back to the main menu.

The use of liquid chemistry in this way greatly improves the specificity of the device as the selected chemicals will only produce a pattern of certain colors with a limited set of molecules. Therefore all other molecules, even in large concentration, will not produce the same color pattern over the cycle. For some compounds such as biological agents, only a single reagent may be needed to produce a color. In many cases the fluid acts as a carrier and medium in which an antigen-antibody binding event takes place. In a further embodiment the reaction pad can be divided into three separate fluid channels each in proximity to a specific capsule. In this way three separate color reactions can be produced spatially in a side-by-side configuration rather than in timed sequence. The physical pattern of colors rather than the timed sequence of color development is equally specific for the chemicals of interest.

By way of example for the screening for trace explosives in its simplest embodiment, the user simply swipes the card on the surface to under test, places it into the chemical reader, and the liquid chemistry and calorimetric analysis are all performed and the result displayed within a short time.

Once the sample is collected and the bar code interpreted, the card is inserted into the device. In one preferred embodiment the card contains two embedded capsules that contain relevant chemicals. The color of the pad is recorded by the device as background and for later analysis. The first capsule is activated and any sequence of color changes is recorded. For macroscopic samples a color may develop for certain explosives immediately. For example, the explosive TNB (tri nitro benzene) will produce an orange coloration. One of the advantages of the method is that it can operate with samples ranging from the macroscopic (milligram) level to the trace (nanogram) level. For a trace sample no color will develop initially, but will appear when heat is applied to the reaction pad. For TNB an orange tinge will develop, but for the explosive HMX no color will appear. The second capsule is then activated and the color recorded. For TNB the color will transition from orange to clear. For macroscopic samples of HMX a pink color will appear, however for trace levels there may be no color change. Heat is then added to the reaction pad and as an example, a pink color would develop for trace amounts of HMX.

The color, sequence, and rate of change of development of the colors is specific for each analyte or related group.

Pigments and dirt may easily be collected from a surface and are easily ignored as they do not produce a color change through the cycle. Substances that do change color will do so in a different manner than targeted substances, as they do not belong to the same chemical groups (families) as the explosive.

Figure 2:
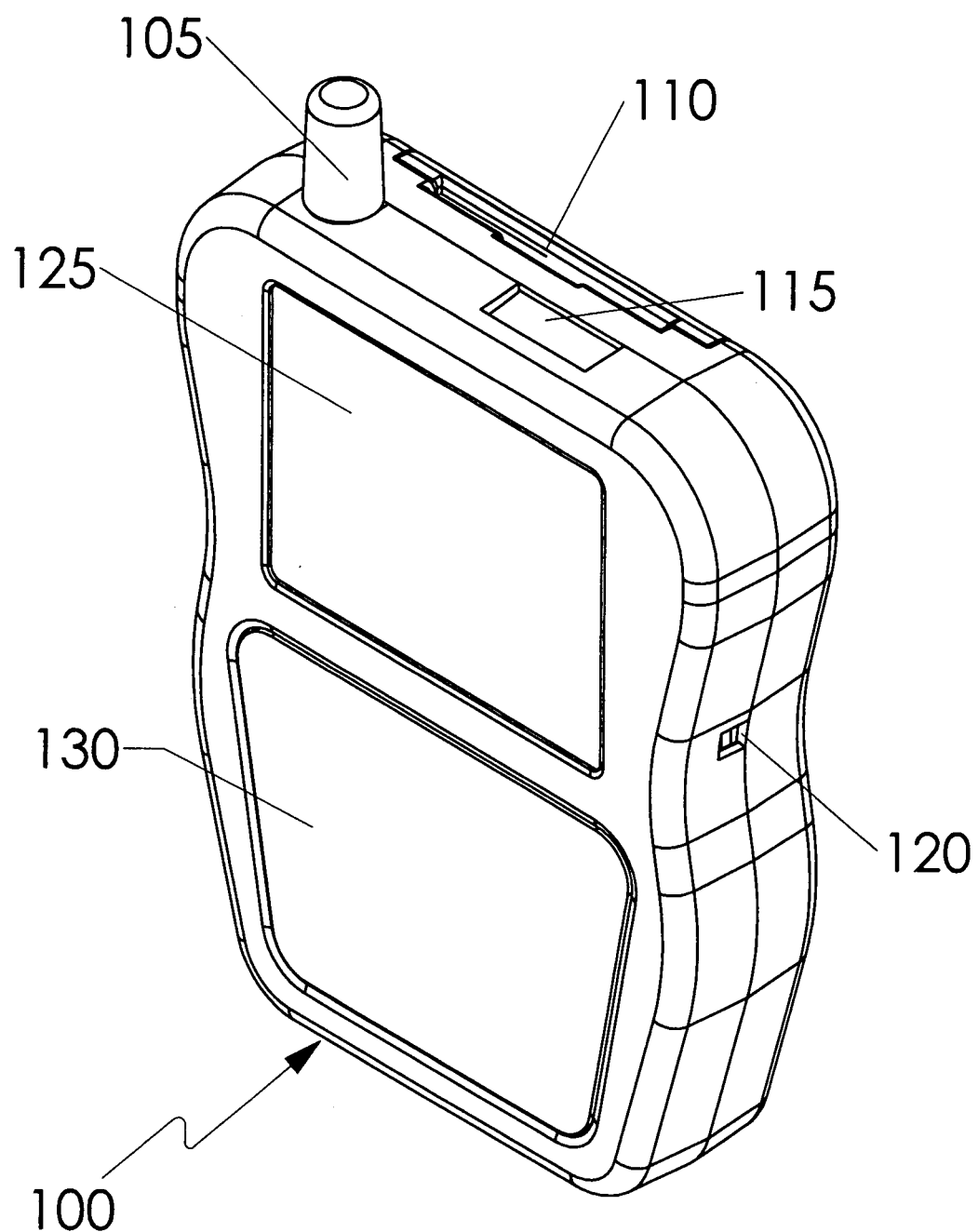
FIG. 2 is an assembled view of the Chemical Detection Unit; an embodiment of the invention.

Now referring to FIG. 2 is an assembled view of the Chemical Detection Unit 100 (CDU), an embodiment of the invention. A Global Positioning System (GPS) or differential GPS antenna 105 captures location of the CDU where the sample is collected. GPS is helpful in the field and the differential GPS is useful when rapid testing is conducted inside confined spaces like buildings or extended compounds. In such confined locations it may be strategically important to map identification of locations where dangerous trace materials may have been detected by the CDU. Likewise, additional antennae may be used for radio communication, Internet communication, computer communication and/or utilizing other communication means. The communication system may further comprise an alarm system to alert/prompt for imminent need for action. There is an ingress door mechanism for card component insertion 110 where the card component, after collecting the sample of the material for testing, is inserted into the CDU. There is an optical window 115 for transmission of barcode scanning laser. The bar code may be coded for individual card component and may contain information as to the type of test and other identification information as desired. The CDU may be battery powered, or powered with other external power sources. A power entry port 120 for use with external direct current power source is provided. A liquid crystal display 125 for software user interface is provided. Also provided are keypad selection buttons 130 for user interaction with the CDU.

Figure 3:
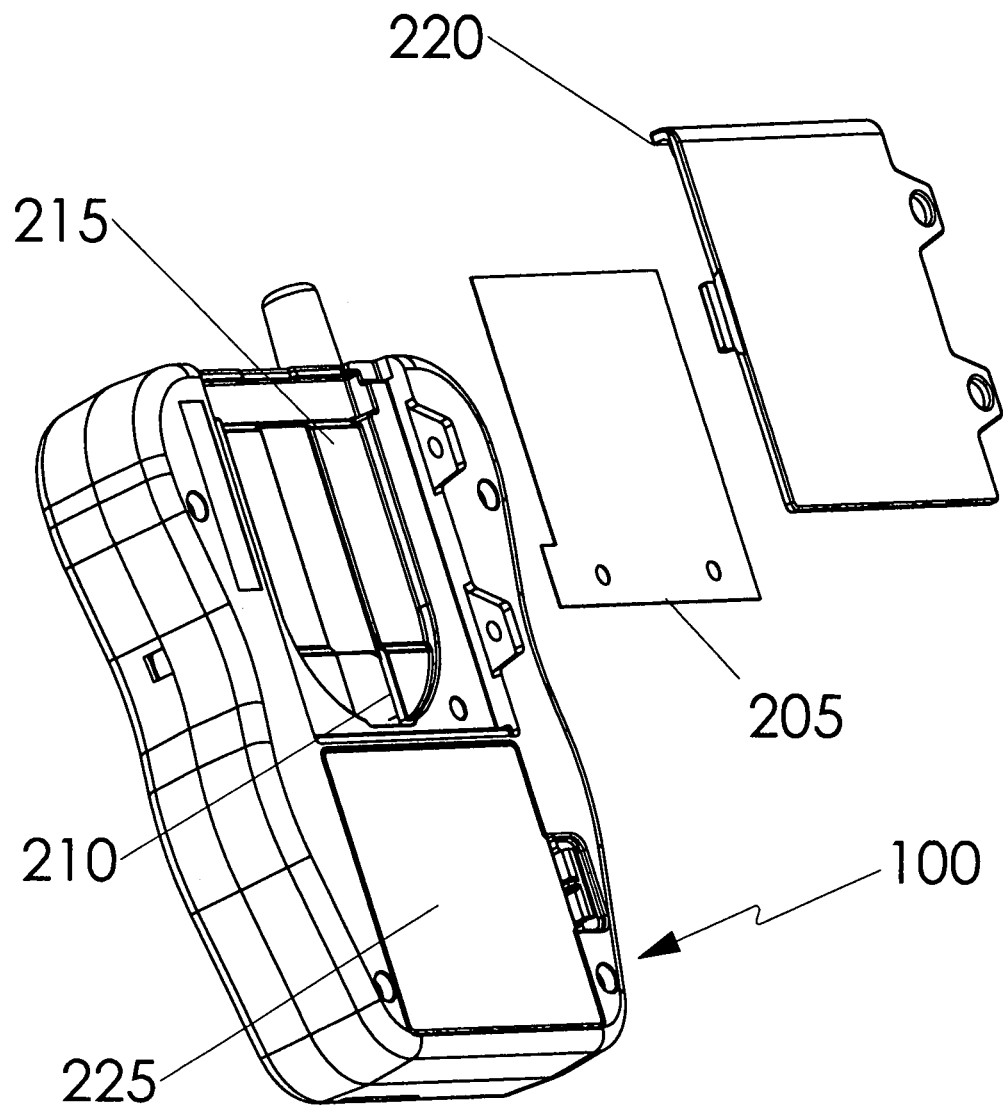
FIG. 3 shows an exploded view of the underside of the Chemical Detection Unit with Optical Reading Chamber.

Now referring to FIG. 3 is the Exploded View of the underside of the Chemical Detection Unit with Optical Reading Chamber. There is a heating element 205 for applying heat to specific regions of the card component. An opening 210 allows optical electronics to view color changes on the pad of the card component. A raised surface 215 applies compressive force to the liquid reagent capsules within card component when the card component is inserted in the CDU, causing the walls of the capsules to yield and allow chemicals in the capsules to establish fluid flow communication with the card component through the channels or wicks or a combinations thereof. A removable panel 220 allows service access to the card ingress cavity. A removable panel 225 provides user access to battery compartment for battery replacement.

Figure 3A:
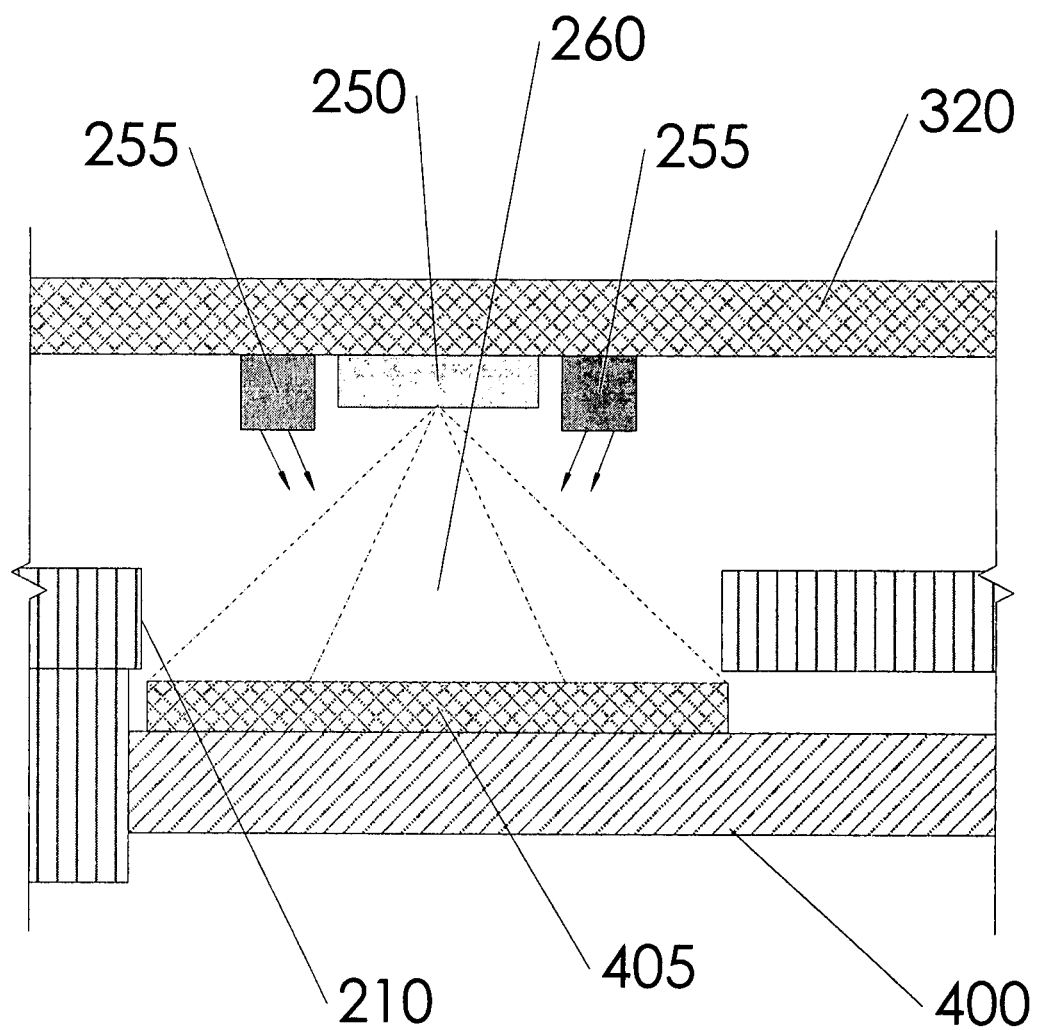
FIG. 3A shows a diagram of optics electronics configuration for color detection.

Referring to FIG. 3A shows a diagram of optics electronics configuration 250 for color detection. Light emitting diodes 255 illuminate the pad with various colors of light to allow for color measurements by the optical sensor on viewing area of the optical pad 260. The mechanical location of the optical sensor is optimized to allow the sensor to measure color only on the sample collection pad, but to also fully encompass the surface of the sample collection pad. The remaining numbered items are described in other figures and are shown here to provide relative location of the components.

Figure 4:
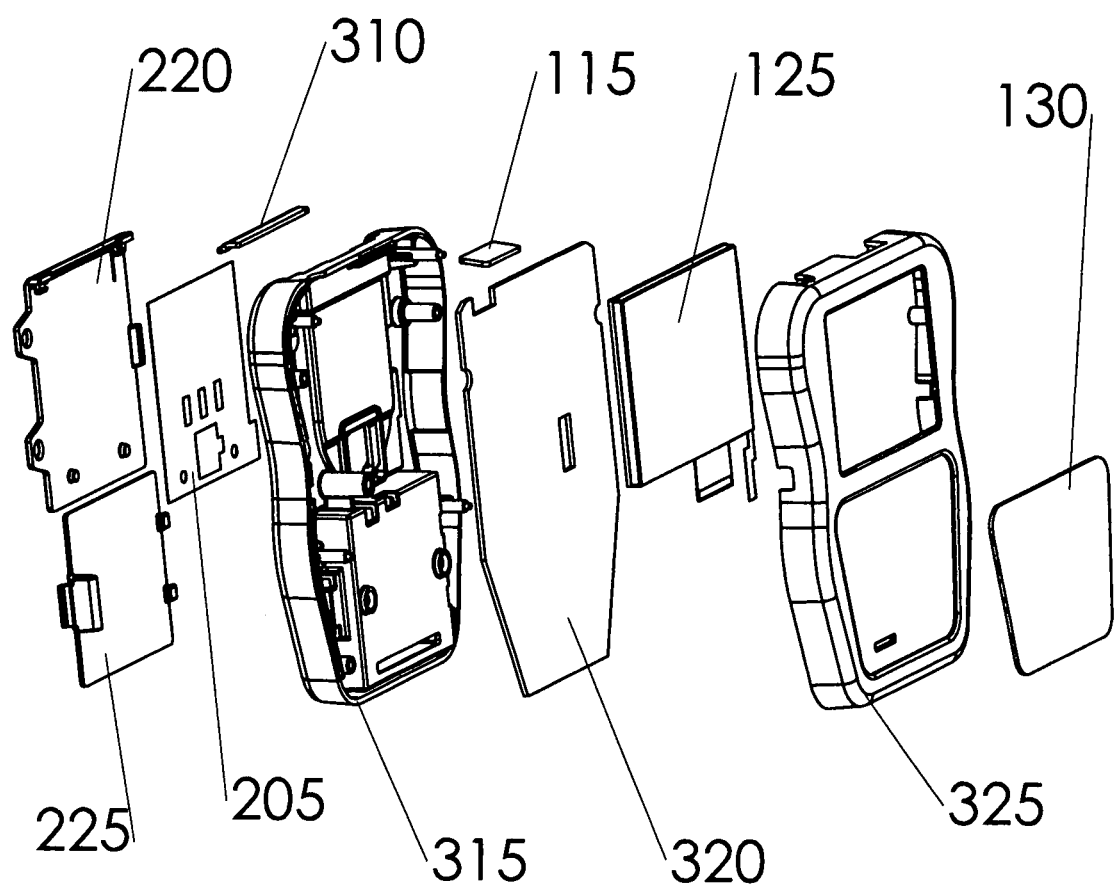
FIG. 4 shows an exploded view of a Handheld Chemical Detection Unit.

With reference to FIG. 4 is an Exploded View of a handheld version of the Chemical Detection Unit, CDU. A hinged door 310 allows card component entry to the card ingress cavity. Bottom half of chemical detection unit enclosure 315 encloses the CDU bottom part. A printed circuit board 320 supports the electronics of the chemical detection unit. The electronics control exposure of the optical instrumentation for detection of the spectral pattern, heating of the card component, and other device subsystems. Top half of chemical detection apparatus enclosure 325 encloses the CDU and further supports keypad 130. In addition, the optical array has multiple pairs of illuminating source and detectors permitting separate zones of the pad to be measured individually, increasing both the range of possible tests and the sensitivity of the unit. As an example of the above, security personnel can test for trace explosives on a bag or vehicle outside an airport terminal. The accurate time, date and location is automatically recorded with the detection results and this information can be transmitted to a central location instantly.

The barcode reader could also be used to collect information from specific sites or objects separately labeled. By way of example a barcode could be placed in a specific location such that when the Chemical Detector Unit is placed in front of it to read the code, it provides location and orientation information. Subsequently, other barcodes could be placed in strategic locations to provide further information.

By way of example, a "first responder" could enter a building whereby scanning of a specifically located barcode provides the starting point for tracking position. Upon entering another floor additional barcodes attached at specific locations could provide information regarding that location within a building.

In a further embodiment of the device the Chemical Detection Unit includes a "radio frequency identification", or RFID, reader. RFID tags attached at specific locations could be read as the device approached, providing location information. Another example would be to replace the barcode scanner and associated procedures and utilize RFID tags implanted into the card component for card identification.

In further embodiments of the device the card can be placed into a separate apparatus to enhance sample collection. Examples include a wand, permitting the card to be swiped behind a cupboard or hard to reach location, an air concentrator device which could collect particles in the air and propel them onto the swipe area, or the card itself could be incorporated into the body of a box cutter type blade and slid into cardboard boxes, sheetrock walls, or other penetrable surfaces.

In further embodiments of the device the Chemical Detection Unit could incorporate a radiation detection sensor or toxic vapor detection sensor of which there are many variations. The detailed invention is the subject of a separate application. By way of example this device could continuously monitor for other toxic and radiation hazards while simultaneously being used to detect trace chemicals.

In a further embodiment of the device, the wireless Bluetooth feature could be paired with a common headset typically used for cellular telephone applications. This headset would provide audible resources to the user, and also allow the user to record audio for storage on the device. An example would be to play back to the user a stored audio recording of a chemical description associated with a test result. Another example would be to permit the operator to record vocal notes to be stored along with the test results in the device. Further examples would be for use with the help system for audio instructions, or for step-by-step feedback from the device to the operator during use.

In a further embodiment of the device, electronic capabilities will be included to communicate over various wireless communication networks. These networks would include, but are not limited to, digital cellular phone networks (EDGE, CDMA, etc.), IEEE 802.11x (Wi-Fi) networks, Zigbee, and SMS text networks. An example would be to send an SMS text to a central reporting location after each positive detection of an explosive. Another example would be to send result and GPS location data over the internet to a data center which could map positive results from clusters of devices to geolocate 'hot spot' regions to better focus military resources into a given geographical area.

In further embodiments of the device, the Bluetooth wireless networking feature could be used to form a personal area network (PAN) to communicate location and result data among multiple devices or to a central base station. This base station could be fitted with a printer and other peripherals, which would allow for group use of multiple devices in facilities with pre-existing security procedures to allow for replacement of existing trace detection systems. Another example would be for multiple devices to function in a 'team' mode for transmitting messages, test results, audio communication and geo-location among preset groups of devices.

In further embodiments of the device, peripheral devices will be connected wirelessly via Bluetooth. An example of this would be a portable radiation detector, which would integrate into the user interface of the device to expand the detection capabilities of the device. As an additional example, the radiation detection and GPS positioning would allow for directional determination of radiation sources. By measuring the radiation strength at multiple locations, one could direct the user towards the radioactive source. When using the 'team' pairing mode of multiple CDU devices, additional source, direction and magnitude measurements would be compiled to increase the accuracy of the radiation source location.

Figure 5:
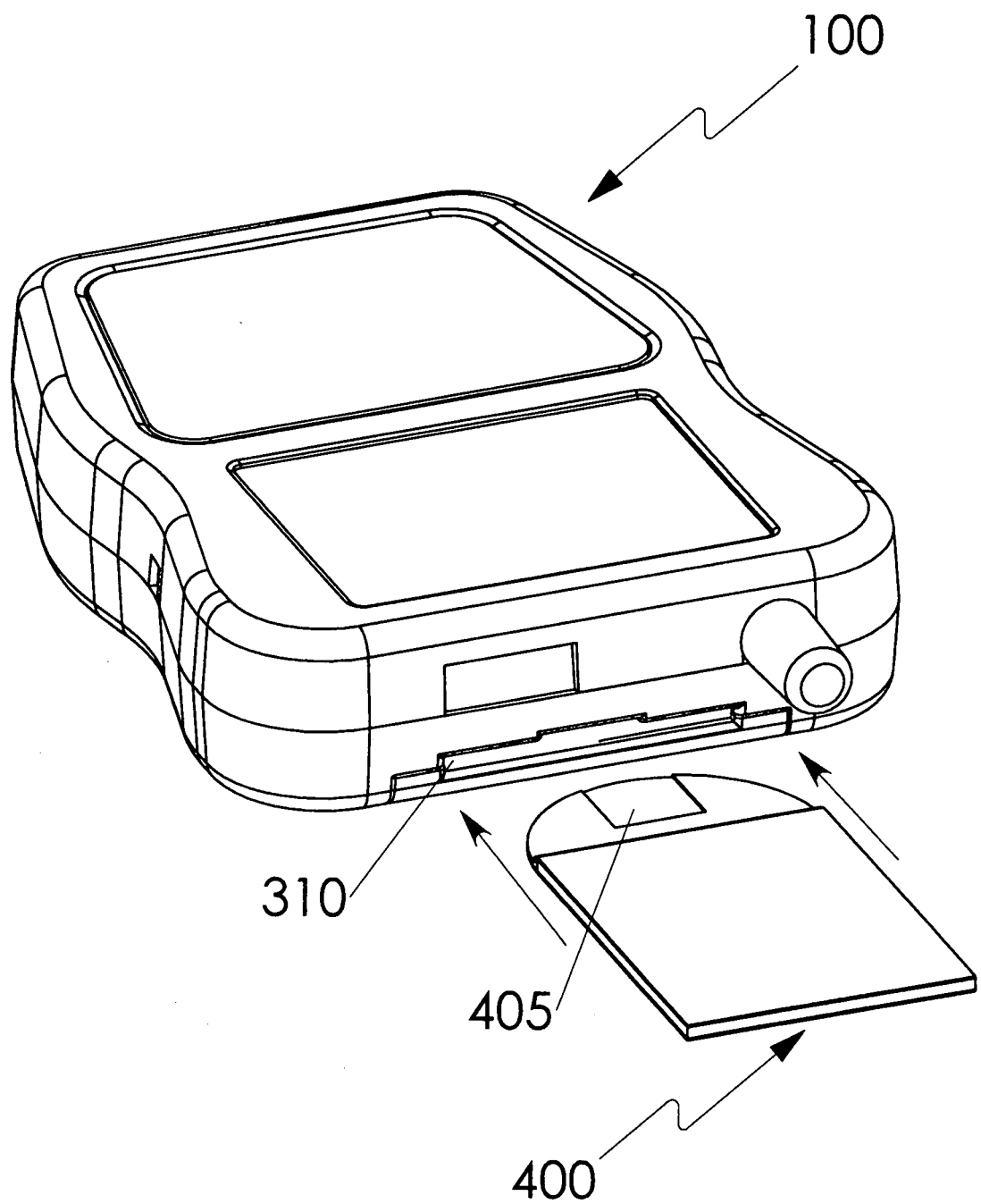
FIG. 5 shows the chemical detection unit with Card Component showing ingress to Optical Reading Chamber

With reference to FIG. 5 shows the direction of entry of the card component 400 in the CDU 100 through the hinged door 310 of the card ingress cavity. The sample collection pad of card component entry direction is as depicted in FIG. 5.

Figure 6:
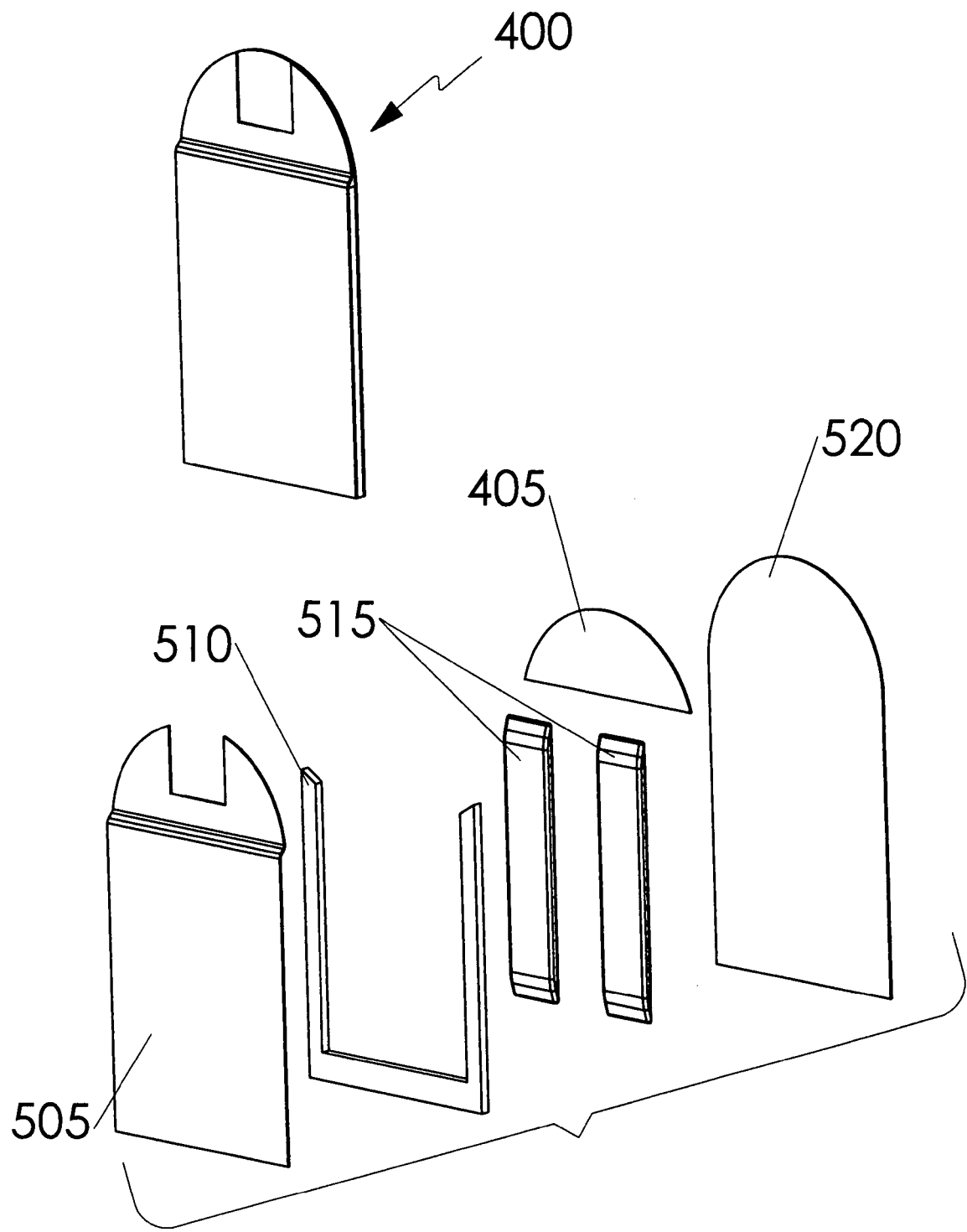
FIG. 6 shows an exploded view of the Card Component.

Now referring to FIG. 6 shows an exploded view of the card component 400 of the invention. A top card layer of card component 505 has a notched cutout for sample collection pad 405. An Inner layer 510 of card component supports the flexible walled capsules 515 wherein the capsules hold various liquid chemical reagents. A backing layer 520 covers the backside of the card component.

Figure 7:
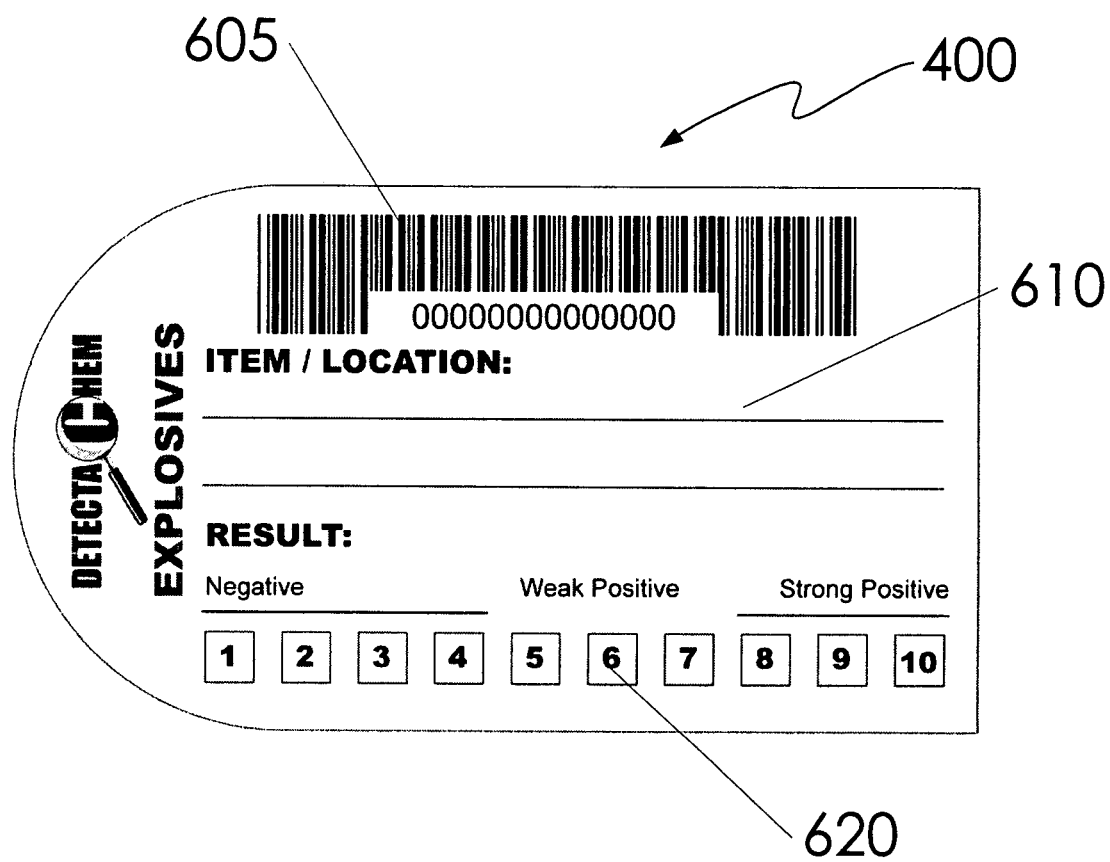
FIG. 7 shows the reverse side view of the Card Component, with user assisting features.

With reference to FIG. 7 shows the top view of the card component 400. Each card component has a unique barcode 605. The bar code is used for identification of the type of test, 'shelf-life' aging of internal chemicals, unique identifier, and any other parameters that a user may wish to associate with the test. A writable surface 610 is provided for user notation on the card component. A readable identifier 615 of the card type (i.e. Explosives, Narcotics, etc.) allows the user to ascertain the type of test being conducted. Another writable surface 620 with selection boxes provides for user recording of test results. Color gradient strip 625 is associated with test result selection boxes, with, for example, green colors corresponding to a negative detection result and red colors representing a positive detection result. This test result gradient is used as a visual cue for the user to correlate the test result numeric value with the interpretation of that numeric value.

The foregoing disclosure and description of the preferred embodiments are illustrative and explanatory thereof, and various changes in the components, elements, configurations, and signal connections, as well as in the details of the illustrated apparatus and construction and method of operation may be made without departing from the spirit and scope of the invention and within the scope of the claims.

What is claimed is:

1. A method of detecting unknown materials from a surface of interest, the method comprising:
   a. collecting an unknown materials sample comprising the unknown materials on a pad of a card component, wherein the collecting comprises swiping the pad on the surface of interest;
   b. initiating a reaction of the unknown materials sample collected on the pad with liquid reagents contained in at least one reagent releasable capsule, wherein the at least one reagent releasable capsule is embedded in the card component and comprises at least one liquid reagent, wherein the reaction is initiated after coupling the pad with a chemical detection unit, and wherein the coupling of the pad with the chemical detection unit causes a wall of the at least one reagent releasable capsule to yield to fluid flow to establish fluid communication between the at least one reagent releasable capsule and the pad;
   c. stimulating the reaction of the unknown materials sample with the at least one liquid reagent to generate at least one spectral pattern of color, wherein the at least one spectral pattern of color corresponds to the unknown materials; and
   d. associating the at least one spectral pattern of color with materials in a database to determine the unknown materials.

2. The method of claim 1, wherein the establishment of the fluid communication between the least one reagent releasable capsule and the pad comprises a disruption of a wall of the least one reagent releasable capsule upon the coupling of the pad with the chemical detection unit, wherein the disruption of the wall of the least one reagent releasable capsule comprises a mechanical puncturing of the wall.

3. The method of claim 1, wherein the stimulating comprises an application of heat to the pad to enhance the reaction.

4. The method of claim 1, further comprising a step of utilizing an optical instrument in the chemical detection unit to detect the at least one spectral pattern of color and store data related to the at least one spectral pattern of color.

5. The method of claim 4, wherein the at least one spectral pattern of color comprises the human visible spectrum, ultraviolet regions of the electromagnetic spectrum, and infrared regions of the electromagnetic spectrum.

6. The method of claim 4, wherein the optical instrument in the chemical detection unit comprises light emitting diodes and an optical sensor, and wherein the light emitting diodes illuminate the pad with various colors of light to allow for color measurements by the optical sensor.

7. The method of claim 4, further comprising a step of displaying detection results on a display unit of the chemical detection unit.

8. The method of claim 4, wherein the associating comprises analyzing the stored data utilizing a comparison algorithm.

9. The method of claim 1, wherein the chemical detection unit is a hand held chemical detection unit.

10. The method of claim 1, wherein the stimulating occurs inside the chemical detection unit.

* * * * *